US008079756B2

(12) United States Patent  (10) Patent No.: US 8,079,756 B2
Quinn et al.  (45) Date of Patent: Dec. 20, 2011

(54) TEMPERATURE PATCH

(75) Inventors: David E. Quinn, Auburn, NY (US);
Scott A. Martin, Warners, NY (US);
John A. Lane, Weedsport, NY (US);
Clare L. Corcoran, Clay, NY (US);
Craig M. Meyerson, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 12/942,066

(22) Filed: Nov. 9, 2010

(65) Prior Publication Data

US 2011/0051774 A1 Mar. 3, 2011

Related U.S. Application Data

(63) Continuation of application No. 11/873,046, filed on Oct. 16, 2007, now Pat. No. 7,857,507, which is a continuation-in-part of application No. 11/678,657, filed on Feb. 26, 2007, now Pat. No. 7,815,367, which is a continuation-in-part of application No. 10/989,631, filed on Nov. 16, 2004, now Pat. No. 7,572,056.

(51) Int. Cl.
*G01J 5/00* (2006.01)
(52) U.S. Cl. ......... 374/121; 374/100; 374/208; 600/574
(58) Field of Classification Search .................. 600/549, 600/474; 116/200, 216; 340/870.17; 702/136, 702/139; 250/338.1
See application file for complete search history.

(56) References Cited

U.S. PATENT DOCUMENTS

| 1,363,259 | A | 12/1920 | Mills |
| 3,533,399 | A | 10/1970 | Goldberg et al. |
| 3,626,757 | A | 12/1971 | Benzinger |
| 3,703,892 | A | 11/1972 | Meyers |
| 3,738,173 | A | 6/1973 | Sato |
| 3,738,479 | A | 6/1973 | Sato |
| 3,837,772 | A | 9/1974 | Van de Walker et al. |
| 3,880,282 | A | 4/1975 | Naumann |
| 3,999,434 | A | 12/1976 | Yen |
| 4,008,614 | A | 2/1977 | Turner |
| 4,054,057 | A | 10/1977 | Kluge et al. |

(Continued)

FOREIGN PATENT DOCUMENTS

FR 2851333 A1 8/2004

(Continued)

OTHER PUBLICATIONS

International Search Report for International Application No. PCT/US2005/038936, Mailed May 4, 2006, (3 pages).

(Continued)

*Primary Examiner* — Gail Verbitsky
(74) *Attorney, Agent, or Firm* — Sonny Z. Zhan

(57) ABSTRACT

A patch may be adapted for placement proximate to a surface region of a mammal. The patch may include an infrared target for receiving thermal energy from the surface region and for emitting infrared radiation according to a substantially known emissivity property. When the target is placed proximate to the surface region, the characteristics of infrared radiation emitted by the target substantially correspond to the temperature of the surface region. The patch may have means for selectively maintaining the target in a position proximate to a surface region of a mammal. The patch may include indicia uniquely associated with the patch.

20 Claims, 4 Drawing Sheets

U.S. PATENT DOCUMENTS

| | | | |
|---|---|---|---|
| 4,086,813 A | 5/1978 | Meek et al. | |
| 4,112,762 A | 9/1978 | Turner | |
| 4,343,185 A | 8/1982 | Knute | |
| 4,433,637 A | 2/1984 | Buirley et al. | |
| 4,457,633 A | 7/1984 | Andrews | |
| 4,588,306 A | 5/1986 | Burger et al. | |
| 4,859,079 A | 8/1989 | Wickersheim et al. | |
| 5,159,936 A | 11/1992 | Yelderman et al. | |
| 5,165,798 A | 11/1992 | Watanabe | |
| 5,169,234 A | 12/1992 | Bohm | |
| 5,325,863 A | 7/1994 | Pompei et al. | |
| 5,340,215 A | 8/1994 | Makita et al. | |
| 5,645,349 A | 7/1997 | Fraden | |
| 5,678,566 A * | 10/1997 | Dribbon | 600/592 |
| 5,874,736 A | 2/1999 | Pompei | |
| 5,893,833 A | 4/1999 | Pompei et al. | |
| 5,983,124 A | 11/1999 | Carr | |
| 6,036,361 A | 3/2000 | Gregory et al. | |
| 6,045,257 A | 4/2000 | Pompei et al. | |
| D423,956 S | 5/2000 | Chen | |
| 6,056,435 A | 5/2000 | Pompei | |
| 6,086,247 A | 7/2000 | von Hollen | |
| 6,129,673 A | 10/2000 | Fraden | |
| 6,191,339 B1 * | 2/2001 | Gueret | 602/58 |
| 6,241,384 B1 | 6/2001 | Pompei et al. | |
| 6,292,685 B1 | 9/2001 | Pompei | |
| 6,299,347 B1 | 10/2001 | Pompei | |
| 6,347,243 B1 | 2/2002 | Fraden | |
| 6,390,671 B1 | 5/2002 | Tseng | |
| 6,402,371 B2 | 6/2002 | Pompei et al. | |
| 6,447,160 B1 | 9/2002 | Fraden | |
| 6,461,037 B1 | 10/2002 | O'Leary | |
| 6,499,877 B2 | 12/2002 | Pompei | |
| 6,527,439 B1 | 3/2003 | Bellifemine | |
| 6,569,189 B1 | 5/2003 | Augustine et al. | |
| 6,595,911 B2 | 7/2003 | LoVuolo | |
| 6,604,854 B1 | 8/2003 | Limburg et al. | |
| 6,609,823 B2 | 8/2003 | Kraus et al. | |
| 6,629,776 B2 | 10/2003 | Bell et al. | |
| 6,709,154 B1 | 3/2004 | Janotte | |
| 6,742,927 B2 | 6/2004 | Bellifemine | |
| 6,751,497 B2 | 6/2004 | Fraden | |
| 6,789,936 B1 | 9/2004 | Kraus et al. | |
| 6,830,549 B2 | 12/2004 | Bui et al. | |
| 6,963,772 B2 | 11/2005 | Bloom et al. | |
| 7,037,083 B2 | 5/2006 | O'Neil et al. | |
| 7,048,437 B2 | 5/2006 | Bellifemine | |
| 7,187,960 B2 | 3/2007 | Abreu | |
| 7,213,969 B2 | 5/2007 | Russak et al. | |
| 7,479,116 B2 * | 1/2009 | Yarden et al. | 600/549 |
| 7,490,575 B2 | 2/2009 | Taylor et al. | |
| 7,572,056 B2 | 8/2009 | Lane et al. | |
| 7,597,668 B2 | 10/2009 | Yarden | |
| 7,815,367 B2 | 10/2010 | Lane et al. | |
| 2002/0017997 A1 | 2/2002 | Felkowitz | |
| 2002/0172257 A1 | 11/2002 | Walls et al. | |
| 2003/0149349 A1 | 8/2003 | Jensen | |
| 2003/0210146 A1 | 11/2003 | Tseng | |
| 2004/0076217 A1 | 4/2004 | Lin | |
| 2004/0215098 A1 | 10/2004 | Barton et al. | |
| 2005/0245839 A1 | 11/2005 | Stivoric et al. | |
| 2005/0254549 A1 | 11/2005 | Harr | |
| 2006/0062274 A1 | 3/2006 | Pompei | |
| 2006/0153278 A1 | 7/2006 | Chen et al. | |
| 2007/0189358 A1 | 8/2007 | Lane et al. | |
| 2008/0137709 A1 | 6/2008 | Quinn et al. | |
| 2008/0161715 A1 * | 7/2008 | Stivoric et al. | 600/549 |
| 2009/0010998 A1 | 1/2009 | Marchitto et al. | |
| 2009/0187115 A1 * | 7/2009 | Yarden et al. | 600/549 |
| 2011/0213559 A1 * | 9/2011 | Pollack et al. | 702/19 |

FOREIGN PATENT DOCUMENTS

| | | | |
|---|---|---|---|
| GB | 2075194 A | 11/1981 | |
| JP | 02162220 A | 6/1990 | |
| JP | 03095422 A | 4/1991 | |
| JP | 03279826 A | 12/1991 | |
| JP | 04283632 A | 10/1992 | |
| WO | WO 92/10133 A1 | 6/1992 | |
| WO | WO2006/055214 A1 | 5/2006 | |
| WO | WO2008/105869 A1 | 9/2008 | |
| WO | WO2009/051863 A1 | 4/2009 | |

OTHER PUBLICATIONS

International Search Report and Written Opinion for International Application No. PCT/US2005/038936, mailed May 31, 2007 (7 pages).

International Search Report and Written Opinion for International Application No. PCT/US2008/068004, mailed Jan. 20, 2009 (12 pages).

* cited by examiner

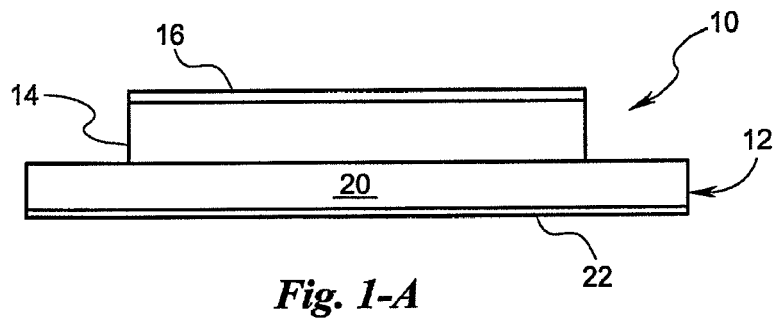
*Fig. 1-A*
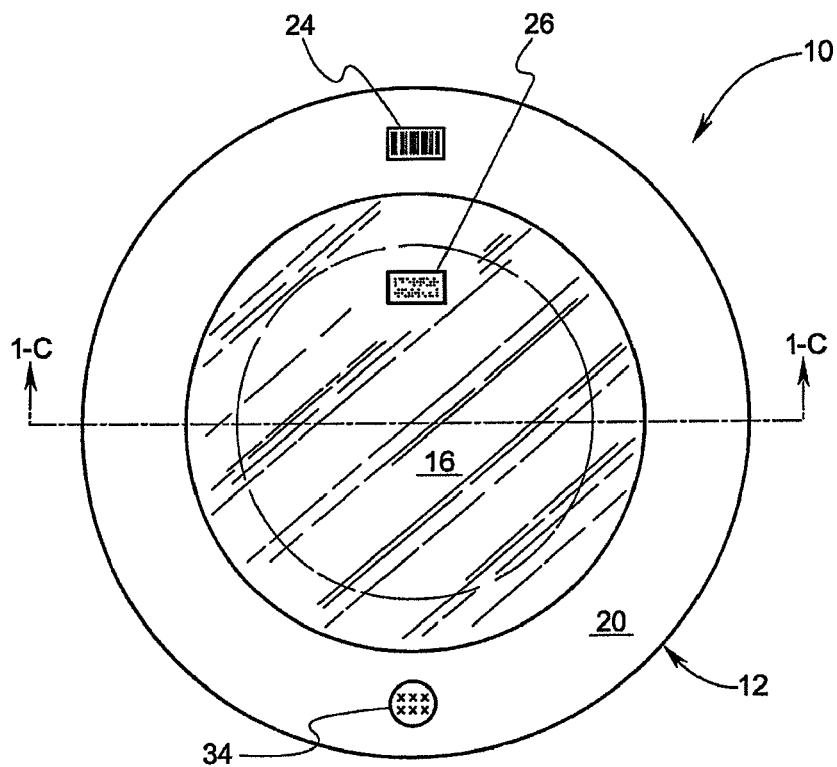
*Fig. 1-B*
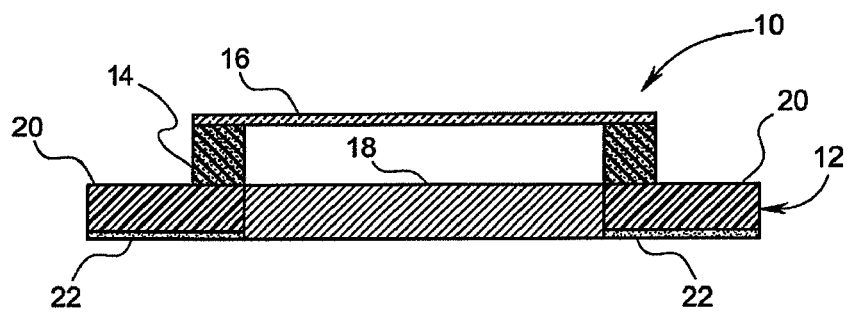
*Fig. 1-C*

Patient Name: Joseph Smith
Patient ID#: ACX2341
Patient Birth Date: 09/22/41
Patient Sex: Male Temperature Patches:
1. Under right bicep
2. Inner left thigh
3. None Bioreactive Agents:
1. None
2. None

Last Readings

| Date | Time | Nurse ID | Temperature | Bioreactive |
|---|---|---|---|---|
| 03/07/07 | 16:34 | B67 | 1. 98.2F | 1. — |
|  |  |  | 2. 98.9F | 2. — |
|  |  |  | 3. — |  |
| 03/07/07 | 13:21 | B22 | 1. 98.6F | 1. — |
|  |  |  | 2. 99.0F | 2. — |
|  |  |  | 3. — |  |
| 03/07/07 | 10:18 | B31 | 1. 98.8F | 1. — |
|  |  |  | 2. 98.6F | 2. — |
|  |  |  | 3. — |  |

Current Nurse ID: B67
Current Date and Time: 03/07/07  19:40

TEMPERATURE PATCH

CROSS-REFERENCE TO RELATED APPLICATIONS

This application is a continuation patent application of, and claims priority and benefit to, co-pending U.S. patent application Ser. No. 11/873,046, that was filed on Oct. 16, 2007 and entitled "Temperature Patch and Method of Using the Same", which is a continuation-in-part application of, and claims the priority and benefit to, U.S. patent application Ser. No. 11/678,657 that was filed Feb. 26, 2007, entitled "Multi-Site Infrared Thermometer", and now issued U.S. Pat. No. 7,815,367, which is a continuation-in-part application of, and claims the priority and benefit to, U.S. patent application Ser. No. 10/989,631 that was filed Nov. 16, 2004, entitled "Probe Cover for Thermometry Apparatus", and now issued U.S. Pat. No. 7,572,056. All of the aforementioned patent applications and patents are incorporated herein by reference in their entirety.

FIELD OF THE INVENTION

This invention relates, in one embodiment, to measuring and/or monitoring body temperature of a mammal, especially a human.

BACKGROUND OF THE INVENTION

The core body temperature of a mammal, especially human, is one of the so-called vital signs that provides a strong indication of the health or medical condition of the mammal. Consequently, accurately assessing the core body temperature, frequently noting the core body temperature, and observing trends in the core body temperature are extremely important criteria in evaluating the medical condition of a mammal and in evaluating whether medical treatments are working desirably or should be implemented.

Traditional thermometers include those materials, both liquid or solid, that expand or otherwise change their physical conformation when heated. Examples include mercury and ethanol based thermometers. Such traditional thermometers usually require long equilibration times which require them to be disposed adjacent to or within orifices of a mammal for long times in order to gain a roughly accurate indication of the core body temperature.

Another disadvantage of traditional thermometers is that their use often causes discomfort to a patient or disrupts a patient's sleep.

It has been known that the body of a mammal radiates infrared radiation, which is generally associated with "heat" being radiated from the body, and which in turn is generally related to the core body temperature of the mammal. Infrared thermometers capable of sensing the infrared ("IR") radiation emitted near the skin or other external surface of a mammal have been utilized to provide a temperature that correlates with the level or amount of IR radiation sensed. Such thermometers, however, are often inaccurate because the level of IR radiation from such a surface may be affected by sources other than the core body temperature, such as the temperature of the air in the vicinity of the surface and the presence of perspiration on the surface, thereby altering the emissivity or reflectivity of the measurement site.

One particularly advantageous location to use an IR thermometer is deep into the inner ear using a so-called tympanic probe, however, the inner ear is often occluded and the ear canal is extremely tortuous, such that the probe often does not reach deep enough into the inner ear to gain an unobstructed sighting in order to obtain an accurate reading. Moreover, the use of such a probe can cause some discomfort to a patient, and often requires that a patient be turned or moved in order to use the probe.

SUMMARY OF THE INVENTION

A patch having an IR target is placed proximate to the surface of a mammal. The patch may include an insulator for protecting the target from exterior, ambient IR radiation and may include bar codes or other indicia uniquely associated with either the patch or the mammal. The patch may also include a bio-reactive agent for indicating characteristics such as the pH of the mammal's skin. The patch may also include a thermometer for sensing the level of IR radiation from the IR target and may include a display of the temperature associated with such a level. The patch may also include a transmitter for wirelessly communicating information about such level to a remote location. A method of using the patch is also disclosed.

BRIEF DESCRIPTION OF THE DRAWINGS

The present invention will be described with reference to the accompanying drawings, wherein:

FIG. 1A is a side schematic illustration of a patch in accordance with one embodiment of the present invention;

FIG. 1B is a top schematic illustration of the patch shown in FIG. 1A;

FIG. 1C is a cross-sectional view of the patch shown in FIG. 1B taken along the lines 1C-1C;

FIG. 4 is a schematic illustration of a display screen that might be utilized in connection with the method of using a patch in accordance with the present invention.

DETAILED DESCRIPTION OF A PREFERRED EMBODIMENT

Figure 2:
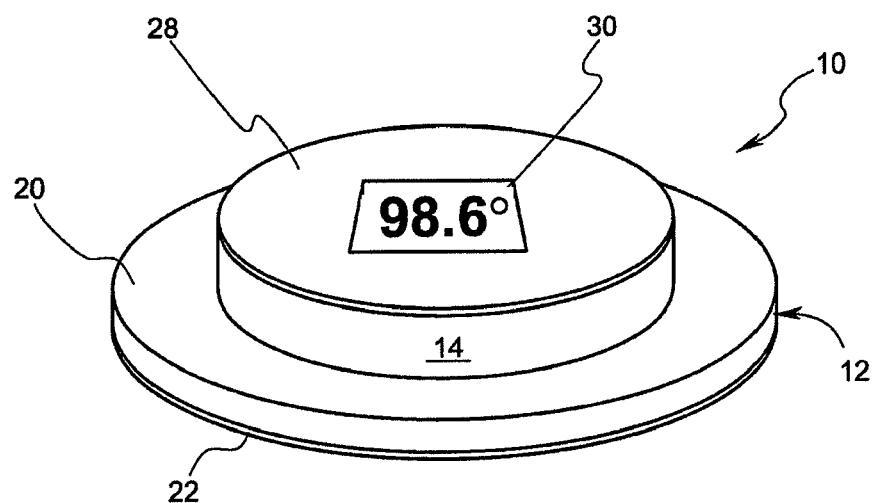
FIG. 2 is a perspective schematic illustration of the patch in accordance with yet another embodiment of the present invention.

Aspects of the present invention will be described with reference to the accompanying drawings wherein like reference numerals refer to the same item. It should be appreciated that the features described herein are exemplary and illustrative only, and that the present invention encompasses both modifications of these features and different features.

There is shown in FIGS. 1A-C a patch 10 constructed in accordance with one embodiment of the present invention. Patch 10 includes a generally disk-shaped base 12 having a circular periphery upon which is centrally mounted an insulator 14 generally configured in the shape of a ring. Patch 10 further includes preferably a sheet or film 16 of material that is transparent preferably to both infrared and visible radiation. The base 12 includes a central disk-shaped core of an infrared target 18 preferably that is co-extensive with the inner annular edge of insulator 14. The base 12 further includes a supporting member 20 preferably fashioned as a ring having an internal peripheral edge that intimately contacts and abuts the peripheral edge of the IR target 18. The patch 10 may also include an adhesive coating or layer 22 disposed along the bottom surface of the supporting member 20 that may be used to selectively secure the patch 10 to the skin or other surface of a mammal. The adhesive coating may, for example, be the same type that is used in connection with either skin bandages or EKG electrodes that are typically placed on the chest of a human for monitoring heart activity.

As especially shown in FIG. 1C, when the patch 10 is placed preferably against the skin of a mammal, the IR target 18 is placed in intimate contact with the skin or other surface. Thermal radiation or energy passes from the body, through its skin or other surface and into the IR target 18 through conduction, convection, or radiation. The IR member 20 then emits infrared radiation according to a known degree of "emissivity" associated with the material from which the IR target 18 is fabricated. The nature of "emissivity" in this patent application relies upon the definition referenced in U.S. Pat. No. 4,659,234 to Brouwer, rather than that referenced in U.S. Pat. No. 7,037,083 to O'Neil. The IR target 18 may be fashioned, for example, from a variety of plastics, paper and other cellulose-based materials, fabric, metal foil, and combinations thereof. Examples of suitable metals include aluminum, brass, copper, and gold. Preferably the IR target material has a relatively high degree of "emissivity", at least about 0.8, 0.9, and, even more preferably, 0.95. Polyethylene film having an "emissivity" of 0.99, has been found especially efficacious.

One factor that influences the rate of heating of the IR target 18 is its mass, which is preferably less than 10.0 milligrams, even more preferably less than about 5.0 milligrams, and even more preferably less than about 1.00 milligrams. Preferably the base 12 is extremely thin, which helps the patch 10 from being obtrusive when operably disposed proximate to the surface of a mammal. Preferably the thickness is in the range of about one one-thousandths to ten one-thousandths of an inch, and very preferably is in the range of about 0.5 one-thousandths to three one-thousandths of an inch. Preferably also the diameter of the IR target 18 is relatively small, within the range of about one-half of an inch to one inch, or stated alternatively, possesses a surface area of about one-fifth to three-quarters of a square inch. However, the invention contemplates that the diameter of the IR target 18 may be larger, for example, three inches or even four inches.

The supporting member 20 may be fashioned of any suitable material, such as polyethylene, polypropylene, starched-based polymers, aluminum, gold plating, and the like. The supporting member 20 may also be formed as a laminate of different materials.

The insulator 14 may be formed of any suitable material, such as a foam, with the material very preferably helping to eliminate the presence of IR radiation within the space defined by the IR target 18, the insulator 14, and the film 16, as best shown in FIG. 1C, from infrared radiation other than that emitted from the IR target 18. The insulator 14 also helps to reduce and minimize the effects of convection or evaporation on the target measurement area. The thickness or height of the insulator 14 as shown in FIGS. 1A and 1C may vary within a wide range, but preferably the overall height or thickness of the patch 10 as shown in FIGS. 1A and 1C is less than about one-sixth of an inch (and thus it will be appreciated that the components of the patch 10 are not necessarily drawn to scale in FIGS. 1A and 1C).

The film 16 is preferably fashioned of a flexible sheet of material that is preferably transparent to both infrared and visible light. It is preferably extremely thin, such as less than about one-thousandths of an inch. The film 16 provides an additional insulating media that helps minimize the presence of IR radiation within the space defined by the film 16, the insulator 14, and the target 18 from sources other than the IR target 18. The film 16 is preferably transparent to IR radiation so that a probe associated with an IR thermometer may be placed near or against the film 16 and detect the IR radiation being emitted by the IR target 18, so as to obtain a reading of the associated temperature of the body of the mammal. It should be appreciated that the present invention contemplates that the film 16 might not be incorporated into the patch 10.

One or more, and preferably all, of the components of the patch 10 are fashioned of flexible materials so that the patch 10 may readily adapt and conform to contour of the surface of the mammal where the patch 10 is to be disposed.

The present invention also contemplates that various indicia may be uniquely associated with the patch 10 such as by printing the indicia on the surface of the patch 10, for example on the upper surface of either the supporting member 20 or the IR target 18 or both. Alternatively the indicia may be disposed on adhesive labels that are affixed to the patch 10, or engraved on the patch, for example. Indicia may, for example, be in the form of a bar code or other pattern capable of being recognized by a machine, an RFID device, a photodiode, a magnetic medium, or physical deformation of a portion of the patch 10, such as by a hole punch pattern or Braille. The indicia may or may not be machine-readable and may or may not be visible to the human eye.

FIG. 1B shows two such indicia 24, 26, with the indicia 24 being placed on the upper surface of the supporting member 20, and the other indicia 26 being disposed on the upper surface of the IR target 18. One of the indicia 24, 26 may be uniquely associated with the patch 10, and the other indicia may be associated with the particular location on the mammal where the patch 10 is to be placed, e.g., under the right bicep (such as where more than one patch is placed proximate to the surface of the same mammal). Preferably one or more of the indicia 24, 26 are placed over the IR target 18, and they are of a character that does not adversely affect the IR emissions of the IR target 18, so that the IR thermometer probe may also be fitted with a mechanism that reads the indicia 24, 26 when taking a reading of the IR radiation emitted from the IR target 18. Alternatively, the indicia may be alpha-numeric and a person operating the IR thermometer probe could manually input the alpha-numeric information into the IR thermometer whereby the same would be associated with the reading of the IR radiation from the IR target 18.

The invention contemplates that the IR thermometer could be a wall-mounted device or a battery-operated hand-held device capable of taking IR radiation readings and indicia readings from one or more patches 10 on the same mammal and taking such readings from patches 10 on different mammals. In this regard, the invention further contemplates that the IR thermometer may be included in a patch 10, as best shown in FIG. 2. Instead of having a film 16, or in addition to having a film 16, the patch 10 may include an IR thermometer 28 that rests as a cap upon the insulator 14 and that preferably possesses a disk shape with a circular periphery co-extensive with the outer peripheral edge of the insulator 14. Alternatively, the thermometer 28 could be set down within the insulator 14, with the peripheral edge of the IR thermometer 28 being co-extensive with and in intimate contact with the inner peripheral edge of the insulator 14 and affixed to the insulator 14 by means of adhesive or other bonding agent, a press fit or snap fit relationship, or other suitable means. The IR thermometer 28 would preferably include a self-contained power source, such as a battery, that could constantly or intermittently sense the IR radiation being emitted by the IR target 18. The invention also contemplates that the IR thermometer 28 may be selectively programmable by means of a computer chip to sense the IR radiation at a selected one of a plurality of time interval frequencies. Additionally, the IR thermometer 28 could also be provided with a device for reading the indicia 24, 26, especially such indicia disposed on the top surface of the IR target 18. The IR thermometer 28 could also include a computer chip programmed with the known "emissivity" of the IR target 18 and for translating the level of IR radiation sensed by the IR thermometer 28 into an associated temperature reading (in Fahrenheit or in Celsius or in another scale) and could further include a display 30 for indicating the associated temperature. Additionally, the IR thermometer 28 could be provided with a programmable chip that translates the indicia into humanly comprehensible information, such as the name of the patient, for example, which also could be revealed in the display 30.

In one embodiment, the information depicted in the display 30 could be scanned by a wall-mounted or hand-held reading device, or alternatively, could be viewed by a human and manually recorded on a chart or manually inputted into an electro-mechanical recording device.

The invention also contemplates that the IR thermometer 28 includes a wireless transmitting device that may be powered by a battery within the IR thermometer 28. The transmitter could transmit to a remote location any or all of the following: the level of IR radiation being sensed by the IR thermometer 28, the correlated temperature associated with that IR level of radiation, the indicia, or the information correlated with the indicia. Such information could be further processed and recorded at the remote location.

The film 16 may be secured to the insulator 14, and the insulator 14 may be secured to the supporting member 20 by means of an adhesive or other bonding agent, thermal fusion, or any other suitable means. The IR target 18 similarly may be attached at its outer peripheral edge to the inner peripheral edge of the supporting member 20 by means of an adhesive or other bonding agent, thermal fusion, a press fit or snap fit relationship, sewn threads, staples, or other similar means. It should be appreciated that the invention contemplates that instead of the IR target 18, the supporting member 20, the insulator 14, and the film 16 having circular peripheral configurations, a wide variety of configurations may be effectively utilized. It should also be appreciated that the invention contemplates that the insulator 14 and the supporting member 20 may be fashioned of the same material. Likewise, it should be appreciated that the IR target 18 may form the entire base 12 and that the base 12 may extend at a variety of different lengths with respect to the outer peripheral edge of the insulator 14.

With regard to the embodiment shown in FIG. 2, it is contemplated that preferably the components of the patch 10 other than the IR thermometer 28 would be relatively inexpensive and disposable, such that they are not re-used, or are limited to a small number of uses (such as to a single patient for a single hospital stay), whereas the IR thermometer 28 itself could be re-used. Also preferably the disposable components are essentially biodegradable. As such, it is contemplated that the IR thermometer 28 could be selectively adhesively attached to either the film 16 or the insulator 14. In another embodiment, the IR thermometer 28 could have fixedly secured thereto either the film 16, or the insulator 14, or both, and then the insulator 14 would be selectively, adhesively secured to the base 12. It should be further understood that, as disclosed in co-pending U.S. patent application Ser. No. 11/678,657, filed on Feb. 26, 2007, such an IR thermometer 28 could be used without any film 16 or insulator 14.

From the foregoing, it should be appreciated that the patch 10 may be placed proximate to various surface regions of a mammal, including those that are comfortable for the mammal as well as those regions that are readily accessible to a nurse, doctor, or other medical practitioner. More than one patch 10 may be placed on the mammal, both so as to provide more than one independent assessment of the body temperature, and so that if the patch 10 is temporarily inaccessible (such as a patient being in a position where the patch 10 is between the patient and an underlying bed), the temperature reading may still be taken without disturbing the patient.

Figure 3:
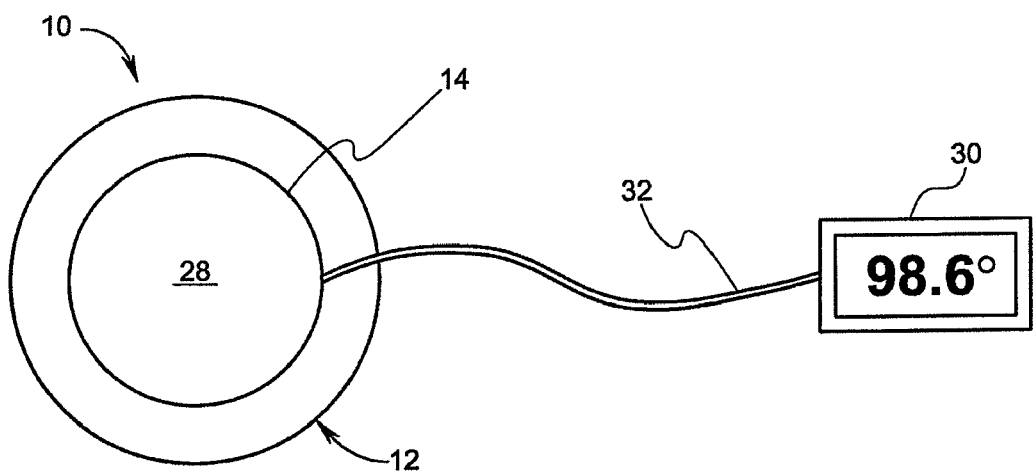
FIG. 3 is a schematic illustration of yet another patch in accordance with an embodiment of the present invention.

As best shown in FIG. 3, in another embodiment of the invention, a patch 10 in all respects similar to that shown in FIG. 2 is depicted on the left side of FIG. 3, however, the display 30 is remotely located with respect to the other components of the patch 10. The display 30 is electronically connected to the IR thermometer 28 in patch 10 by means of a wire 32 or other electrical pathway. In such an embodiment, the patch 10 may be located in a surface region of the mammal that is relatively inaccessible or that inhibits wireless transmission, but, the display 30 could be positioned at a different, more accessible location. The display 30 may be positioned by means of an adhesive, for example, at a different location on the mammal's body.

It is also contemplated that the patch 10 be provided with a bio-reactive agent or material 34, as best shown in FIG. 1B, that is capable of being altered when in the presence of a pre-selected bio-chemical property associated with the surface of the mammal, and where the alteration can be detected either visually or through a machine. Bio-reactive material 34 may be implanted into the IR target 18 or in the supporting member 20 and may extend therethrough so as to be in contact with the skin surface. In a simple example, the bio-reactive 40 may consist of "litmus" paper that changes to one of two colors, depending upon the pH of the liquid or other material in which the bio-reactive material 34 is in contact. The bio-reactive material 34 may be sensitive to and altered by liquid or gas effluents from the mammal's skin, such as perspiration. The bio-chemical components of such effluents may be indicative of certain health or medical conditions of the mammal, which include blood glucose levels, jaundice, lead contamination, turgor, infections, anemia, and the like. The alteration may be detected by spectroscopy, which involves an analysis of the spectral distribution of a known light source after being reflected from the surface of the bio-reactive material 34.

Figure 5:
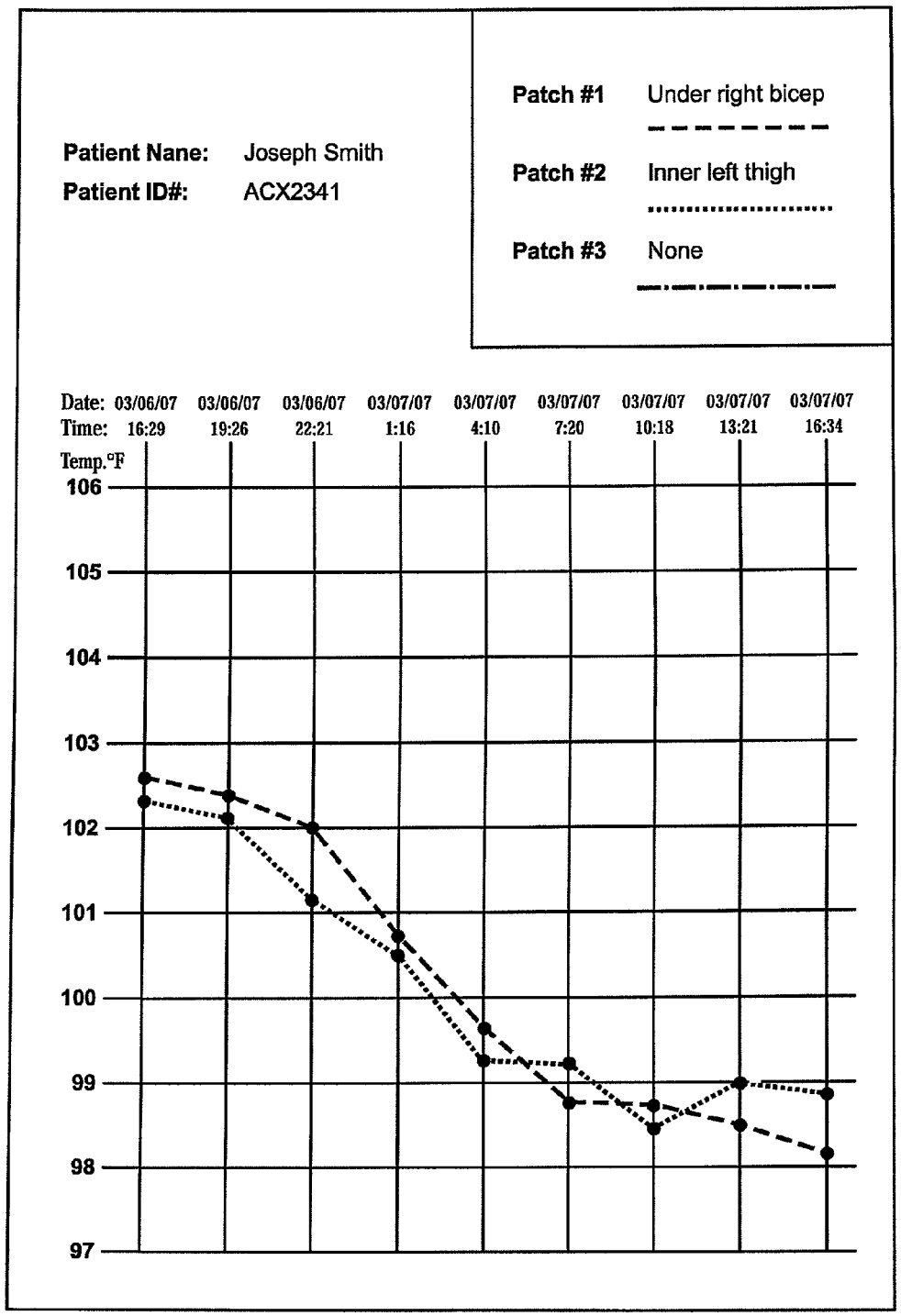
FIG. 5 is a schematic illustration of another display that may be utilized in connection with the method of using a patch in accordance with the present invention.

FIGS. 4 and 5 each show a display of information that may be obtained from a patch 10 in accordance with the present invention. The displays may be on a hand-held device, a wall-mounted device, or on a computer screen at a remote location. In the display shown in FIG. 4, the various information about the patient is disclosed and there is an indication that there are two patches 10 disposed on the patient as well as an indication as to where the patches 10 are located. The display also indicates that there are no patches 10 with bio-reactive agents. The display further indicates the dates and times of the last three temperature (and possibly bio-reactive agent) readings as well as the values of the temperature (and any bio-reactive) readings. Finally, the current nurse I.D. number and the current date and time are given. Such a display is especially efficacious with a hand-held IR thermometer or other device, which helps indicate how many patches 10 are on a patient and where they are located as well as what temperature reading is associated with which patch 10. The nurse I.D. number may be manually inputted into the IR thermometer or other device or may be inputted by reading a bar code or other indicia associated with the nurse, which is then inputted into a computer.

Similarly, FIG. 5 depicts information about the patient as well as a graph (with legend) giving the temperature readings from each of the two patches 10 over the last eight readings as well as the dates and times of those eight readings. It will be appreciated illustratively in FIG. 5 that over about a fifteen hour period (from 16:29 on Mar. 6, 2007 to 7:20 on Mar. 7, 2007), the patient's temperature dropped from approximately 102.5 degrees Fahrenheit to under 99 degrees Fahrenheit. And that over the most recent ten hours, the patient's temperature stabilized between 98 and 99 degrees Fahrenheit. As such, the graph indicates the recent temperature trend of the patient.

While the invention has been described with reference to preferred embodiments, it will be understood by those skilled in the art that various changes may be made and equivalents may be substituted for features thereof to adapt to particular situations without departing from the scope of the invention. Therefore, it is intended that the invention not be limited to the particular embodiments disclosed herein for carrying out the invention.

What is claimed is:

1. A temperature patch comprising:
   a supporting portion;
   an infrared target disposed within said supporting portion for receiving thermal energy from a skin surface region of a mammal and for emitting infrared radiation according to a known emissivity property, when the target is placed onto the skin surface region, in which the characteristics of infrared radiation emitted by the target substantially correspond to the temperature of the surface region;
   an insulator disposed upon said supporting portion and radially coextensive with an outer edge of said infrared target;
   means for selectively maintaining the target in a position on said supporting portion, enabling said target to be sufficiently proximate to the skin surface region to enable thermal energy therefrom to be received; and
   indicia fixedly disposed on said temperature patch, said indicia identifying at least one of said temperature patch and said mammal.

2. The patch according to claim 1 wherein the indicia is one of visible and invisible to a human eye.

3. The patch according to claim 1 wherein the indicia is selected from the group consisting of a bar code or other pattern recognized by at least one of a machine, an RFID device, a photodiode, a magnetic medium, and physical deformation of a portion of the patch.

4. The patch according to claim 1 wherein the patch includes a bio-reactive agent having a characteristic that is detectively altered in the presence of a pre-selected bio-chemical property of the skin surface region.

5. The patch according to claim 4 wherein the property is essentially the pH value of the surface region.

6. The patch according to claim 4 wherein the bio-reactive agent characteristic is configured to be altered in a manner detectable through spectroscopy.

7. The patch according to claim 1 further including indicia uniquely associated with a particular location on the mammal where the patch is to be placed.

8. The patch according to claim 1 wherein the target is flexible so as to permit the patch to adapt and conform to the contour of the surface region.

9. The patch according to claim 1 wherein the target and the maintaining means are disposable and are fashioned of essentially biodegradable materials.

10. The patch according to claim 1, wherein said insulator is a ring-shaped member forming an annular space between the emission side of said infrared target and said insulator, said patch further including an infrared transparent film disposed onto said insulator forming an emission window.

11. A temperature patch comprising:
    a supporting portion;
    an infrared target disposed within said supporting portion for receiving thermal energy from the surface region and for outwardly emitting infrared radiation according to a known emissivity property when the target is placed onto a skin surface region of a mammal, in which the characteristics of infrared radiation emitted by the target substantially correspond to the temperature of the skin surface region;
    an insulator disposed on said supporting portion and radially coextensive with an outer edge of said infrared target; and
    indicia fixedly disposed on said temperature patch, said indicia identifying at least one of said patch and said mammal.

12. The patch according to claim 11 wherein the indicia is one of visible and invisible to a human eye.

13. The patch according to claim 11 wherein the indicia is selected from the group consisting of a bar code or other pattern adapted to be recognized by at least one of a machine, an RFID device, a photodiode, a magnetic medium, and physical deformation of a portion of the patch.

14. The patch according to claim 11 wherein the patch includes a bio-reactive agent having a characteristic that is configured to be detectively altered in the presence of a pre-selected bio-chemical property of the skin surface region.

15. The patch according to claim 14 wherein the property is essentially the pH value of the surface region.

16. The patch according claim 14 wherein the bio-reactive agent characteristic is altered in a manner detectable through spectroscopy.

17. The patch according to claim 11 further including indicia uniquely associated with a particular location on the mammal where the patch is to be placed.

18. The patch according to claim 11 wherein the target is flexible, enabling so as to permit the patch to adapt and conform to the contour of the skin surface region.

19. The patch according to claim 11 wherein the target is adapted to be disposable and fashioned of a essentially biodegradable material.

20. The patch according to claim 11, wherein said insulator is a ring-shaped member forming an annular space between an emission side of said infrared target and said insulator, said patch further including an infrared transparent film disposed onto said insulator forming an emission window.

* * * * *